US012773348B2

(12) United States Patent
Gliner et al.

(10) Patent No.: US 12,773,348 B2
(45) Date of Patent: Oct. 27, 2026

(54) INTRAOCULAR PRESSURE CONTROL SYSTEM

(71) Applicant: JOHNSON & JOHNSON SURGICAL VISION, INC., Irvine, CA (US)

(72) Inventors: Vadim Gliner, Haifa (IL); Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 911 days.

(21) Appl. No.: 17/958,493

(22) Filed: Oct. 3, 2022

(65) Prior Publication Data

US 2024/0108503 A1 Apr. 4, 2024

(51) Int. Cl.
*A61F 9/007* (2006.01)
*A61M 1/00* (2006.01)

(52) U.S. Cl.
CPC ........... *A61F 9/00745* (2013.01); *A61M 1/73* (2021.05); *A61M 1/777* (2021.05)

(58) Field of Classification Search
CPC ........ A61M 1/77; A61M 1/772; A61M 1/774; A61M 1/777; A61M 1/73; A61M 2210/0612; A61M 2205/3341; A61M 2205/3344; A61F 9/00745; A61F 9/00736
See application file for complete search history.

(56) References Cited

U.S. PATENT DOCUMENTS 2,094,830 A 10/1937 David
2,842,331 A 7/1958 Anderson
3,393,566 A 7/1968 Malcolm et al.
3,575,301 A 4/1971 Panissidi
(Continued)

FOREIGN PATENT DOCUMENTS

AU 2013202059 A1 4/2013
CN 108323001 A 7/2018
(Continued)

OTHER PUBLICATIONS

Bello S., et al., "Development of a Smart Pump for Monitoring and Controlling Intraocular Pressure," Annals of Biomedical Engineering, Apr. 2017, vol. 45(4), pp. 990-1002.
(Continued)

*Primary Examiner* — Kami A Bosworth
*Assistant Examiner* — Avery Smale

(57) ABSTRACT

In one exemplary mode, a phacoemulsification system includes a phacoemulsification probe, an irrigation tube to provide irrigation fluid into an eye, an irrigation pump to pump irrigation fluid into the eye, an aspiration tube convey aspiration fluid from the eye, an aspiration pump to pump the aspiration fluid from the eye, a sensor to provide a signal indicative of current intraocular pressure in the eye, and a pump controller to receive the signal provided by the sensor, compute a value of intraocular pressure at a future time responsively to the provided signal and an indicator of change in the intraocular pressure over time, and control the irrigation pump to adjust a flow rate of the irrigation fluid to maintain the intraocular pressure at a given intraocular pressure responsively to the computed value of the intraocular pressure at the future time.

18 Claims, 3 Drawing Sheets

(56) References Cited

U.S. PATENT DOCUMENTS

| | | | |
|---|---|---|---|
| 3,920,014 A | 11/1975 | Banko | |
| 3,994,421 A | 11/1976 | Hansen | |
| 4,274,411 A | 6/1981 | Dotson, Jr. | |
| 4,291,706 A | 9/1981 | Voges et al. | |
| 4,384,578 A | 5/1983 | Winkler | |
| 4,555,940 A | 12/1985 | Renger | |
| 4,653,719 A | 3/1987 | Cabrera et al. | |
| 4,680,445 A | 7/1987 | Ogawa | |
| 4,702,733 A | 10/1987 | Wright et al. | |
| 4,818,186 A | 4/1989 | Pastrone et al. | |
| 4,832,685 A | 5/1989 | Haines | |
| 4,902,034 A | 2/1990 | Maguran et al. | |
| 4,935,005 A | 6/1990 | Haines | |
| 4,954,960 A | 9/1990 | Lo et al. | |
| 5,032,111 A | 7/1991 | Morris et al. | |
| 5,047,009 A | 9/1991 | Morris et al. | |
| 5,106,367 A | 4/1992 | Ureche et al. | |
| 5,108,372 A | 4/1992 | Swenson | |
| 5,135,485 A | 8/1992 | Cohen et al. | |
| 5,167,620 A | 12/1992 | Ureche et al. | |
| 5,190,042 A | 3/1993 | Hock | |
| 5,242,404 A | 9/1993 | Conley et al. | |
| 5,328,456 A | 7/1994 | Horiguchi et al. | |
| 5,354,268 A | 10/1994 | Peterson et al. | |
| 5,405,269 A | 4/1995 | Stupecky | |
| 5,417,246 A | 5/1995 | Perkins et al. | |
| 5,429,601 A | 7/1995 | Conley et al. | |
| 5,476,448 A | 12/1995 | Urich | |
| 5,487,827 A | 1/1996 | Peterson et al. | |
| 5,569,188 A | 10/1996 | Mackool | |
| 5,591,127 A | 1/1997 | Barwick, Jr. et al. | |
| 5,616,120 A | 4/1997 | Andrew et al. | |
| 5,649,905 A | 7/1997 | Zanger et al. | |
| 5,693,013 A | 12/1997 | Geuder | |
| 5,695,473 A | 12/1997 | Olsen | |
| 5,697,898 A | 12/1997 | Devine | |
| 5,700,240 A | 12/1997 | Barwick, Jr. et al. | |
| 5,733,256 A | 3/1998 | Costin | |
| 5,766,146 A | 6/1998 | Barwick, Jr. | |
| 5,810,765 A | 9/1998 | Oda | |
| 5,827,223 A | 10/1998 | Butterfield | |
| 5,865,764 A | 2/1999 | Moorhead | |
| 5,885,243 A | 3/1999 | Capetan et al. | |
| 5,910,110 A | 6/1999 | Bastable | |
| 5,921,554 A | 7/1999 | Derian et al. | |
| 5,935,106 A | 8/1999 | Olsen | |
| 6,050,496 A | 4/2000 | Hefler | |
| 6,083,193 A | 7/2000 | Kadziauskas et al. | |
| 6,159,175 A | 12/2000 | Strukel et al. | |
| 6,167,588 B1 | 1/2001 | Dyson | |
| 6,170,383 B1 | 1/2001 | Mauritz | |
| 6,179,808 B1 | 1/2001 | Boukhny et al. | |
| 6,190,354 B1 | 2/2001 | Sell et al. | |
| 6,383,203 B1 | 5/2002 | Makihara | |
| 6,423,029 B1 | 7/2002 | Elsberry | |
| 6,491,661 B1 | 12/2002 | Boukhny et al. | |
| 6,533,747 B1 | 3/2003 | Polaschegg et al. | |
| 6,565,535 B2 | 5/2003 | Zaias et al. | |
| 6,579,255 B2 | 6/2003 | Kadziauskas et al. | |
| 6,599,271 B1 | 7/2003 | Easley | |
| 6,648,223 B2 | 11/2003 | Boukhny et al. | |
| 6,681,730 B1 | 1/2004 | Koneda et al. | |
| 6,740,058 B2 | 5/2004 | Lal et al. | |
| 6,780,166 B2 | 8/2004 | Kanda et al. | |
| 6,986,753 B2 | 1/2006 | Bui | |
| 7,083,591 B2 | 8/2006 | Cionni | |
| 7,146,864 B2 | 12/2006 | Sullivan et al. | |
| 7,297,137 B2 | 11/2007 | Gordon et al. | |
| 7,670,330 B2 | 3/2010 | Claus et al. | |
| 7,695,447 B2 | 4/2010 | Khashayar et al. | |
| 7,785,336 B2 | 8/2010 | Staggs | |
| 7,811,255 B2 | 10/2010 | Boukhny et al. | |
| 8,246,580 B2 | 8/2012 | Hopkins et al. | |
| 8,380,126 B1 | 2/2013 | Ma et al. | |
| 8,425,452 B2 | 4/2013 | Claus et al. | |
| 8,430,840 B2 | 4/2013 | Nazarifar et al. | |
| 8,430,841 B2 | 4/2013 | Claus et al. | |
| 8,444,592 B2 | 5/2013 | Williams et al. | |
| 8,479,585 B2 | 7/2013 | Shaw-klein | |
| 8,491,528 B2 | 7/2013 | Muri et al. | |
| 8,523,812 B2 | 9/2013 | Boukhny et al. | |
| 8,617,106 B2 | 12/2013 | Zacharias | |
| 8,652,086 B2 | 2/2014 | Gerg et al. | |
| 8,668,665 B2 | 3/2014 | Gerg et al. | |
| 8,715,220 B2 | 5/2014 | Gerg et al. | |
| 8,721,594 B2 | 5/2014 | Zacharias | |
| 9,198,798 B2 | 12/2015 | Claus et al. | |
| 9,482,563 B2 | 11/2016 | Calderin et al. | |
| 9,549,851 B2 | 1/2017 | Chon et al. | |
| 9,610,193 B2 | 4/2017 | Velasco et al. | |
| 9,610,913 B2 | 4/2017 | Narita | |
| 9,782,232 B1 | 10/2017 | Papac | |
| 9,795,507 B2 | 10/2017 | Hajishah et al. | |
| 9,861,522 B2 | 1/2018 | Sorensen et al. | |
| 9,931,447 B2 | 4/2018 | Layser et al. | |
| 10,125,877 B2 | 11/2018 | Morgan et al. | |
| 10,182,940 B2 | 1/2019 | Chandrakant et al. | |
| 10,278,861 B2 | 5/2019 | Bourne | |
| 10,463,780 B2 | 11/2019 | Mallough et al. | |
| 10,470,926 B2 | 11/2019 | Zacharias | |
| 10,500,319 B2 | 12/2019 | Banko | |
| 10,518,005 B2 | 12/2019 | Carr et al. | |
| 10,702,415 B2 | 7/2020 | Charles | |
| 11,033,897 B2 | 6/2021 | Szita et al. | |
| 11,051,978 B2 * | 7/2021 | Heeren | A61M 3/0283 |
| 11,071,816 B2 | 7/2021 | Mehta et al. | |
| 11,185,623 B2 | 11/2021 | Ovchinnikov et al. | |
| 11,383,020 B2 | 7/2022 | Keh et al. | |
| 11,446,424 B2 | 9/2022 | Mehta et al. | |
| 11,602,586 B2 | 3/2023 | Bourne et al. | |
| 2001/0023331 A1 | 9/2001 | Kanda et al. | |
| 2002/0019607 A1 | 2/2002 | Bui | |
| 2002/0174910 A1 | 11/2002 | Willeke et al. | |
| 2002/0193817 A1 | 12/2002 | Lal et al. | |
| 2003/0006729 A1 | 1/2003 | Raymond | |
| 2003/0050613 A1 | 3/2003 | Hammerslag | |
| 2003/0050619 A1 | 3/2003 | Mooijman et al. | |
| 2003/0078487 A1 | 4/2003 | Jeffries et al. | |
| 2003/0105437 A1 | 6/2003 | Neubert | |
| 2004/0092885 A1 | 5/2004 | Duchon et al. | |
| 2004/0092921 A1 | 5/2004 | Kadziauskas et al. | |
| 2004/0101445 A1 | 5/2004 | Shvets et al. | |
| 2005/0054971 A1 | 3/2005 | Steen et al. | |
| 2005/0080375 A1 | 4/2005 | Kadziauskas et al. | |
| 2005/0096593 A1 | 5/2005 | Pope et al. | |
| 2005/0118048 A1 | 6/2005 | Traxinger | |
| 2005/0181018 A1 | 8/2005 | Peyman | |
| 2005/0209560 A1 | 9/2005 | Boukhny et al. | |
| 2005/0209621 A1 | 9/2005 | Gordon et al. | |
| 2005/0228423 A1 | 10/2005 | Khashayar et al. | |
| 2005/0234441 A1 | 10/2005 | Bisch et al. | |
| 2005/0261628 A1 | 11/2005 | Boukhny et al. | |
| 2005/0261715 A1 | 11/2005 | Boukhny et al. | |
| 2005/0267504 A1 | 12/2005 | Boukhny et al. | |
| 2006/0058811 A1 | 3/2006 | Kishimoto et al. | |
| 2006/0064053 A1 | 3/2006 | Bollish et al. | |
| 2006/0224107 A1 | 10/2006 | Claus et al. | |
| 2006/0224143 A1 | 10/2006 | Claus et al. | |
| 2006/0224163 A1 | 10/2006 | Sutton | |
| 2006/0281986 A1 | 12/2006 | Orilla et al. | |
| 2007/0005029 A1 | 1/2007 | Hopkins et al. | |
| 2007/0227265 A1 | 10/2007 | Sugi et al. | |
| 2007/0270744 A1 | 11/2007 | Dacquay et al. | |
| 2008/0000485 A1 | 1/2008 | Williams et al. | |
| 2008/0015406 A1 | 1/2008 | Dlugos et al. | |
| 2008/0033349 A1 | 2/2008 | Suzuki | |
| 2008/0053560 A1 | 3/2008 | Hartman et al. | |
| 2008/0112828 A1 | 5/2008 | Muri et al. | |
| 2008/0114289 A1 | 5/2008 | Muri et al. | |
| 2008/0114290 A1 | 5/2008 | King et al. | |
| 2008/0125698 A1 | 5/2008 | Gerg et al. | |
| 2008/0154095 A1 | 6/2008 | Stubkjaer et al. | |
| 2008/0177126 A1 | 7/2008 | Tate et al. | |
| 2008/0319374 A1 | 12/2008 | Zacharias | |

(56) References Cited

U.S. PATENT DOCUMENTS

| | | | |
|---|---|---|---|
| 2008/0319451 | A1 | 12/2008 | Zacharias |
| 2009/0013780 | A1 | 1/2009 | Gao et al. |
| 2009/0048607 | A1 | 2/2009 | Rockley |
| 2009/0158855 | A1 | 6/2009 | Holden |
| 2009/0163863 | A1 | 6/2009 | Lutwyche |
| 2009/0302671 | A1 | 12/2009 | Brooks |
| 2010/0030134 | A1 | 2/2010 | Fitzgerald et al. |
| 2010/0111735 | A1 | 5/2010 | Tu |
| 2010/0121257 | A1 | 5/2010 | King |
| 2010/0125246 | A1 | 5/2010 | Kalpin |
| 2010/0130915 | A1 | 5/2010 | Claus et al. |
| 2010/0145302 | A1 | 6/2010 | Cull et al. |
| 2010/0174238 | A1 | 7/2010 | Sher |
| 2010/0185150 | A1 | 7/2010 | Zacharias |
| 2010/0249693 | A1 | 9/2010 | Links |
| 2010/0280435 | A1 | 11/2010 | Raney et al. |
| 2010/0292631 | A1 | 11/2010 | Holden |
| 2010/0312170 | A1 | 12/2010 | Maaskamp et al. |
| 2011/0027118 | A1 | 2/2011 | Milovanovic |
| 2011/0087156 | A1 | 4/2011 | Claus |
| 2011/0092891 | A1 | 4/2011 | Gerg et al. |
| 2011/0092896 | A1 | 4/2011 | Kuebler et al. |
| 2011/0112472 | A1 | 5/2011 | Jacobson et al. |
| 2011/0152728 | A1 | 6/2011 | Teodorescu |
| 2011/0257591 | A1 | 10/2011 | Nelson Konen et al. |
| 2011/0284777 | A1 | 11/2011 | Pitchford et al. |
| 2011/0295191 | A1 | 12/2011 | Injev |
| 2011/0313343 | A1 | 12/2011 | Milutinovic et al. |
| 2012/0004595 | A1 | 1/2012 | Dubois et al. |
| 2012/0041362 | A1 | 2/2012 | Gerg et al. |
| 2012/0265144 | A1 | 10/2012 | Kalpin et al. |
| 2013/0060210 | A1 | 3/2013 | Ross et al. |
| 2013/0060211 | A1 | 3/2013 | Adams, Jr. |
| 2013/0062543 | A1 | 3/2013 | Shiao et al. |
| 2013/0123680 | A1 | 5/2013 | Ha et al. |
| 2013/0131578 | A1 | 5/2013 | Stalmans et al. |
| 2013/0150782 | A1 | 6/2013 | Sorensen et al. |
| 2013/0197471 | A1 | 8/2013 | Williams et al. |
| 2013/0246079 | A1 | 9/2013 | Hoffman et al. |
| 2014/0100518 | A1 | 4/2014 | Baxter et al. |
| 2014/0107459 | A1 | 4/2014 | Lind et al. |
| 2014/0114236 | A1 | 4/2014 | Gordon et al. |
| 2014/0114237 | A1 | 4/2014 | Gordon |
| 2014/0163455 | A1 | 6/2014 | Wilson et al. |
| 2014/0171869 | A1 | 6/2014 | Zhang |
| 2014/0206940 | A1 | 7/2014 | Hufford |
| 2014/0257172 | A1 | 9/2014 | Yalamanchili |
| 2014/0282018 | A1 | 9/2014 | Amble et al. |
| 2014/0323953 | A1 | 10/2014 | Sorensen et al. |
| 2014/0364799 | A1 | 12/2014 | Beauvais et al. |
| 2015/0057524 | A1 | 2/2015 | Artsyukhovich et al. |
| 2015/0157501 | A1 | 6/2015 | Bourne et al. |
| 2015/0359666 | A1 | 12/2015 | Zacharias |
| 2016/0128869 | A1 | 5/2016 | Zacharias |
| 2016/0175578 | A1 | 6/2016 | Roholt |
| 2016/0220751 | A1 | 8/2016 | Mallough et al. |
| 2016/0346123 | A1 | 12/2016 | Koplin |
| 2016/0367735 | A1 | 12/2016 | Eddo et al. |
| 2017/0022488 | A1 | 1/2017 | Bermudez et al. |
| 2017/0224888 | A1 | 8/2017 | Hickey et al. |
| 2017/0246419 | A1 | 8/2017 | Callaghan et al. |
| 2017/0312431 | A1 | 11/2017 | Johnson et al. |
| 2017/0326000 | A1 | 11/2017 | Heeren et al. |
| 2017/0333253 | A1 | 11/2017 | Heeren et al. |
| 2017/0367885 | A1 | 12/2017 | Bourne |
| 2017/0367887 | A1 | 12/2017 | Muri et al. |
| 2018/0028359 | A1 | 2/2018 | Gordon et al. |
| 2018/0049220 | A1 | 2/2018 | Patil et al. |
| 2018/0049920 | A1 | 2/2018 | Charles |
| 2018/0078415 | A1 | 3/2018 | Citterio et al. |
| 2018/0092774 | A1 | 4/2018 | Mehta et al. |
| 2018/0279876 | A1 | 10/2018 | Paschalis |
| 2018/0296738 | A1 | 10/2018 | King et al. |
| 2018/0304012 | A1 | 10/2018 | Jansen |
| 2018/0318131 | A1 | 11/2018 | Boukhny et al. |
| 2018/0338861 | A1* | 11/2018 | Hallen .................. A61M 5/142 |
| 2019/0099526 | A1 | 4/2019 | Hajishah et al. |
| 2019/0099529 | A1 | 4/2019 | Mehta et al. |
| 2019/0099546 | A1 | 4/2019 | Keh et al. |
| 2019/0099547 | A1* | 4/2019 | Mehta .................... A61M 1/74 |
| 2019/0099548 | A1 | 4/2019 | Mehta et al. |
| 2019/0133822 | A1 | 5/2019 | Banko |
| 2019/0143008 | A1 | 5/2019 | Brundage et al. |
| 2019/0176557 | A1 | 6/2019 | Marking et al. |
| 2019/0200885 | A1 | 7/2019 | Jacobsen |
| 2019/0262175 | A1 | 8/2019 | Kerkhoff et al. |
| 2019/0282401 | A1 | 9/2019 | Sorensen et al. |
| 2019/0365567 | A1 | 12/2019 | Balkenbush et al. |
| 2020/0030147 | A1 | 1/2020 | Koplin |
| 2020/0107958 | A1 | 4/2020 | Wong et al. |
| 2020/0337900 | A1 | 10/2020 | Nazarifar et al. |
| 2020/0360594 | A1 | 11/2020 | Dam-huisman |
| 2021/0106734 | A1 | 4/2021 | Mehta et al. |
| 2021/0153741 | A1 | 5/2021 | Berdahl et al. |
| 2021/0353145 | A1 | 11/2021 | Kamthan et al. |
| 2021/0386927 | A1 | 12/2021 | Mehta et al. |
| 2021/0386928 | A1 | 12/2021 | Mehta et al. |
| 2022/0133537 | A1 | 5/2022 | Govari et al. |
| 2022/0192876 | A1 | 6/2022 | Algawi et al. |
| 2022/0192877 | A1 | 6/2022 | Algawi et al. |
| 2022/0193322 | A1 | 6/2022 | Govari et al. |
| 2023/0190525 | A1 | 6/2023 | Yan et al. |
| 2023/0390478 | A1 | 12/2023 | Fung et al. |
| 2024/0115421 | A1 | 4/2024 | Govari et al. |
| 2024/0207092 | A1 | 6/2024 | Govari |

FOREIGN PATENT DOCUMENTS

| | | | |
|---|---|---|---|
| CN | 116250982 | A | 6/2023 |
| DE | 19753636 | A1 | 9/1999 |
| DE | 20318275 | U1 | 2/2004 |
| EP | 0997363 | A2 | 5/2000 |
| EP | 1382291 | A2 | 1/2004 |
| EP | 1471342 | A2 | 10/2004 |
| EP | 1900347 | A1 | 3/2008 |
| EP | 1471342 | B1 | 8/2009 |
| EP | 2320842 | A2 | 5/2011 |
| EP | 2379126 | A2 | 10/2011 |
| EP | 2320842 | B1 | 6/2012 |
| EP | 2164435 | B1 | 8/2012 |
| EP | 2919850 | B1 | 10/2018 |
| JP | S62500640 | A | 3/1987 |
| JP | 2001161740 | A | 6/2001 |
| JP | 2003225247 | A | 8/2003 |
| RU | 2720821 | C1 | 5/2020 |
| WO | 8906522 | A2 | 7/1989 |
| WO | 9945868 | A1 | 9/1999 |
| WO | 0194893 | A1 | 12/2001 |
| WO | 03047653 | A1 | 6/2003 |
| WO | 2004108189 | A2 | 12/2004 |
| WO | 2004110524 | A2 | 12/2004 |
| WO | 2005037156 | A1 | 4/2005 |
| WO | 2007143797 | A1 | 12/2007 |
| WO | 2008030872 | A1 | 3/2008 |
| WO | 2008157674 | A1 | 12/2008 |
| WO | 2009076717 | A1 | 6/2009 |
| WO | 2009076717 | A9 | 8/2009 |
| WO | 2010124755 | A1 | 11/2010 |
| WO | 2011045033 | A1 | 4/2011 |
| WO | 2011105909 | A1 | 9/2011 |
| WO | 2014151209 | A1 | 9/2014 |
| WO | 2016122790 | A1 | 8/2016 |
| WO | 2016148754 | A1 | 9/2016 |
| WO | 2016150754 | A1 | 9/2016 |
| WO | 2016191665 | A1 | 12/2016 |
| WO | 2017044138 | A1 | 3/2017 |
| WO | 2018033877 | A1 | 2/2018 |
| WO | 2018064625 | A1 | 4/2018 |
| WO | 2019068151 | A1 | 4/2019 |

(56) References Cited

FOREIGN PATENT DOCUMENTS

| | | |
|---|---|---|
| WO | 2019115584 A1 | 6/2019 |
| WO | 2021083938 A1 | 5/2021 |

OTHER PUBLICATIONS

Cionni R.J., "Evaluating Two Key Safety Advances In the Centurion Vision System," ALCON, Cataract and Refractive Surgery Today, Aug. 2019, 4 pages.
Gopesh T., et al., "Rapid and Accurate Pressure Sensing Device for Direct Measurement of Intraocular Pressure," Translational Vision Science and Technology (TVST), Feb. 2020, vol. 9 (3), Article 28, pp. 1-9.
Miller et al., "Millennial Eye", Supplement to Contract & Refractive Surgery Today, pp. 1-16, Sep./Oct. 2019.
Thomas_et_al, "Phaco Machine basics", Pearls in Ophthalmology, 5 pages, Jul. 17, 2010.
Yao et al., "A Flexible and Highly Sensitive Piezoresistive Pressure Sensor Based on Micropatterned Films Coated with Carbon Nanotubes", Journal of Nanomaterials, pp. 1-6, 2016.

* cited by examiner

INTRAOCULAR PRESSURE CONTROL SYSTEM

FIELD OF THE DISCLOSURE

The present disclosure relates to phacoemulsification systems, and in particular, but not exclusively to, intraocular pressure control in phacoemulsification systems.

BACKGROUND

A cataract is a clouding and hardening of the eye's natural lens, a structure which is positioned behind the cornea, iris, and pupil. The lens is mostly made up of water and protein and as people age these proteins change and may begin to clump together obscuring portions of the lens. To correct this a physician may recommend phacoemulsification cataract surgery. Before the procedure, the surgeon numbs the area with anesthesia. Then a small incision is made in the sclera or clear cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract while a pump aspirates lens particles and fluid from the eye through the tip. The pump is typically controlled with a microprocessor.

Any suitable pump may be used, for example, a peristaltic and/or a venturi type of pump. Aspirated fluids are replaced with irrigation of a balanced salt solution to maintain the anterior chamber of the eye. After removing the cataract with phacoemulsification, the softer outer lens cortex is removed with suction. An intraocular lens (IOL) is introduced into the empty lens capsule. Small struts called haptics hold the IOL in place. Once correctly installed the IOL restores the patient's vision.

BRIEF DESCRIPTION OF THE DRAWINGS

The present disclosure will be understood from the following detailed description, taken in conjunction with the drawings in which.

DESCRIPTION OF EXAMPLES

Overview

Figure 1:
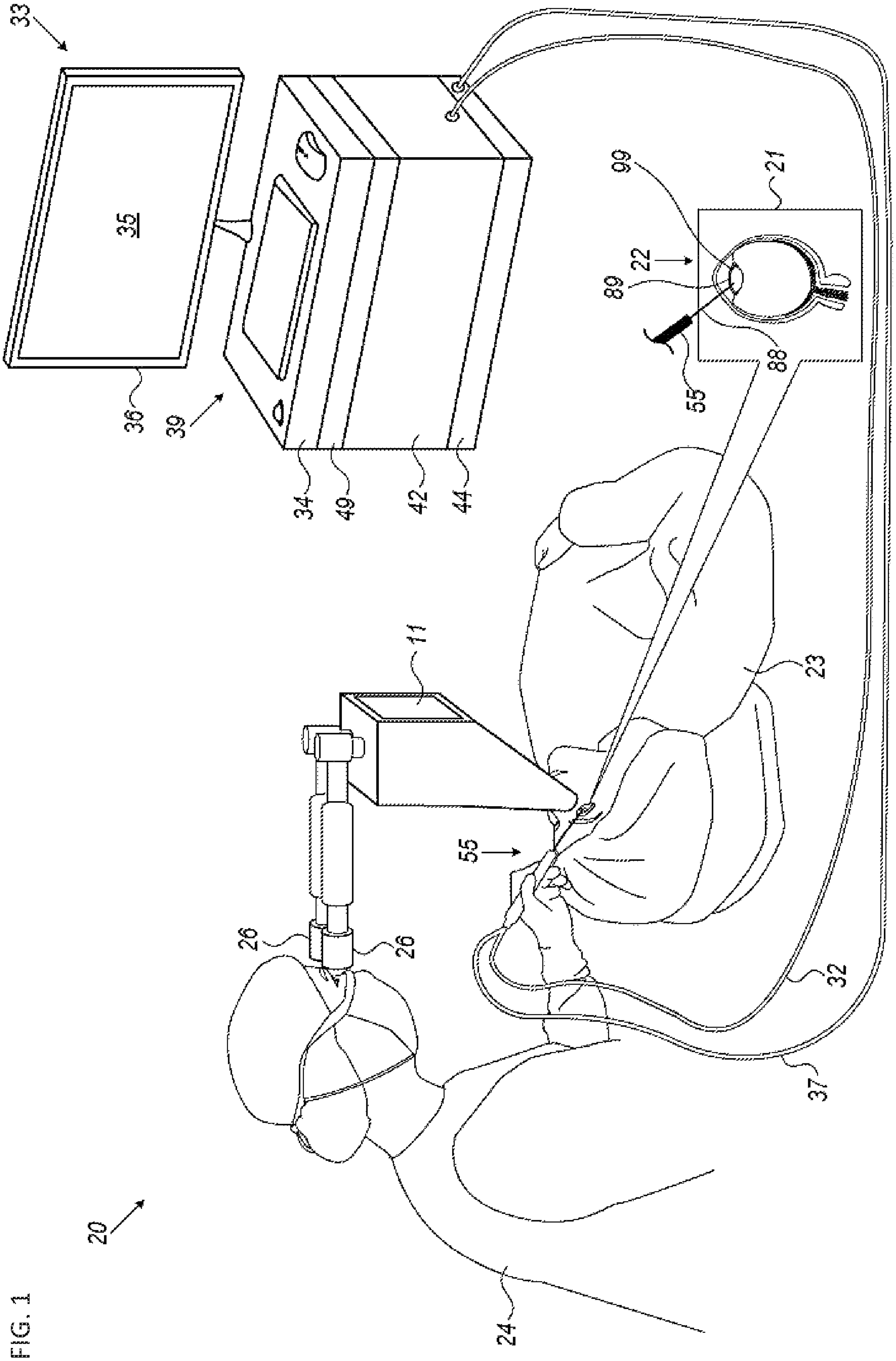
FIG. 1 is a schematic pictorial illustration of an ophthalmic surgical system constructed and operative in accordance with an exemplary mode of the present disclosure.

During phacoemulsification, fluid and cataract particles are aspirated from the eye and irrigation fluid is directed into the eye to replace lost fluid and maintain a stable eye pressure. It is typically desired to control the irrigation and aspiration flow in a manner that maintains a steady IOP (intraocular pressure). The balance between aspiration and irrigation is a fine balance which needs to be maintained to prevent intraocular pressure (TOP) exceeding safe limits. Both too much and too little IOP may be dangerous for the eye.

For example, if aspiration is increased to remove cataract particles from the eye, irrigation also needs to be increased.

The flow controller managing the aspiration and irrigation pumps may have difficulty in maintaining a very steady IOP (without fluctuations). Using a pressure sensor to monitor the IOP and adjusting the irrigation pump rate according to the monitored IOP may help. However, it takes time for the irrigation pump to achieve the adjusted flow rate and for the new pump rate to be propagated along the irrigation tubing. By the time the desired flow rate is achieved, the IOP may have changed so that the present adjustment is no longer suitable.

In some exemplary modes, a trend in the IOP is monitored during a phacoemulsification procedure and used to predict the IOP forward going (e.g., 100 milliseconds from the current time). The IOP at a future time is predicted (e.g., computed) based on the current IOP as provided by a pressure sensor close to the eye (e.g., in an irrigation channel of the phacoemulsification probe), or in the eye (e.g., on another probe inserted into the eye), and one or more indicators as how the IOP is changing or will change over time. The predicted IOP for the future time is then used to determine a desired flow rate for the irrigation pump to maintain the actual IOP at, or around, a given IOP. In some exemplary modes, a controller for the pumps includes a PID controller having control parameters which are set based on the predicted IOP and the given IOP at which the actual IOP should be maintained. In some exemplary modes, the ability to predict the future IOP may be enhanced by the flexible irrigation tubing smoothing the changes in IOP.

Indicators of how the IOP is changing may include one or more of the following: a flow rate of the aspiration fluid (which may be assumed to be equal to the rate of the aspiration pump); a rate of change of the flow rate of the aspiration fluid; a change of the intraocular pressure over time; and a rate of change of the intraocular pressure over time. In some exemplary modes, for smooth changes in TOP (below a threshold gradient), the prediction may be expected to provide improved results. If the current slope of the IOP is above the threshold gradient, this predictive feature may be turned off.

In some exemplary modes, if the IOP is changing too quickly, the predicted IOP may not be an accurate reflection of the actual future IOP and therefore, the predictive feature may be turned off.

System Description

Reference is now made to FIG. 1, which is a schematic pictorial illustration of an ophthalmic surgical system 20, in accordance with an exemplary mode of the present disclosure. System 20 is configured to carry out various types of ophthalmic procedures, such as cataract surgery.

In some exemplary modes, system 20 comprises a medical instrument, in the present example a phacoemulsification handpiece, also referred to herein as a tool 55, used by a surgeon 24 to carry out the cataract surgery. In other exemplary modes, system 20 may comprise other surgical tools, such as but not limited to an irrigation and aspiration (I/A) handpiece, a diathermy handpiece, a vitrectomy handpiece, and similar instruments.

Reference is now made to an inset 21 showing a sectional view of the surgical procedure carried out in an eye 22 of a patient 23. In some exemplary modes, surgeon 24 applies tool 55 for treating eye 22, and in the present example, surgeon 24 inserts a needle 88 of tool 55 into eye 22. In the example of inset 21, during a cataract surgical procedure, surgeon 24 inserts needle 88 into a capsular bag 89 so as to emulsify a lens 99 of eye 22.

Reference is now made back to the general view of FIG. 1. In some exemplary modes, system 20 comprises a console 33, which comprises a processor 34, a memory 49, a generator 44 and a pumping sub-system 42 configured to apply, via multiple tubes 32, irrigation fluids (not shown) into eye 22 and to draw eye fluids away from eye 22 into pumping sub-system 42. The pumping sub-system includes an irrigation and aspiration pump described in more detail with reference to FIG. 2. In the context of the present disclosure, the term "eye fluid" refers to any mixture of natural eye fluid, irrigation fluid and lens material. Note that tubes 32 may comprise an irrigation tube for supplying the irrigation fluid into eye 22, and a separate aspiration tube for drawing the eye fluids away from eye 22.

In some exemplary modes, generator 44 is electrically connected to tool 55, via a plurality of wires referred to herein as an electrical cable 37. Generator 44 is configured to generate one or more voltage periodic (e.g., sinusoidal) signals, also referred to herein as periodic signals, having one or more frequencies, respectively. Generator 44 is further configured to generate a plurality of driving signals, so as to vibrate needle 88 of tool 55 in accordance with a predefined pattern, so as to emulsify lens 99 of eye 22.

In some exemplary modes, processor 34 typically comprises a general-purpose computer, with suitable front end and interface circuits for controlling generator 44, pumping sub-system 42 and other components of system 20.

In practice, some or all of the functions of the processor 34 may be combined in a single physical component or, alternatively, implemented using multiple physical components. These physical components may comprise hard-wired or programmable devices, or a combination of the two. In some exemplary modes, at least some of the functions of the processor 34 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

In some exemplary modes, system 20 comprises an ophthalmic surgical microscope 11, such as ZEISS OPMI LUMERA series or ZEISS ARTEVO series supplied by Carl Zeiss Meditec AG (Oberkochen, Germany), or any other suitable type of ophthalmic surgical microscope provided by other suppliers. Ophthalmic surgical microscope 11 is configured to produce stereoscopic optical images and two-dimensional (2D) optical images of eye 22. During the cataract surgery, surgeon 24 typically looks though eyepieces 26 of ophthalmic surgical microscope 11 for viewing eye 22.

In some exemplary modes, console 33 comprises a display 36 and input devices 39, which may be used by surgeon 24 for controlling tool 55 and other components of system 20. Moreover, processor 34 is configured to display on display 36, an image 35 received from any suitable medical imaging system for assisting surgeon to carry out the cataract surgery.

This particular configuration of system 20 is shown by way of example, in order to illustrate certain problems that are addressed by exemplary modes of the present disclosure and to demonstrate the application of these exemplary modes in enhancing the performance of such a system. Exemplary modes of the present disclosure, however, are by no means limited to this specific sort of example system, and the principles described herein may similarly be applied to other sorts of ophthalmic and other minimally invasive and surgical systems.

Figure 2:
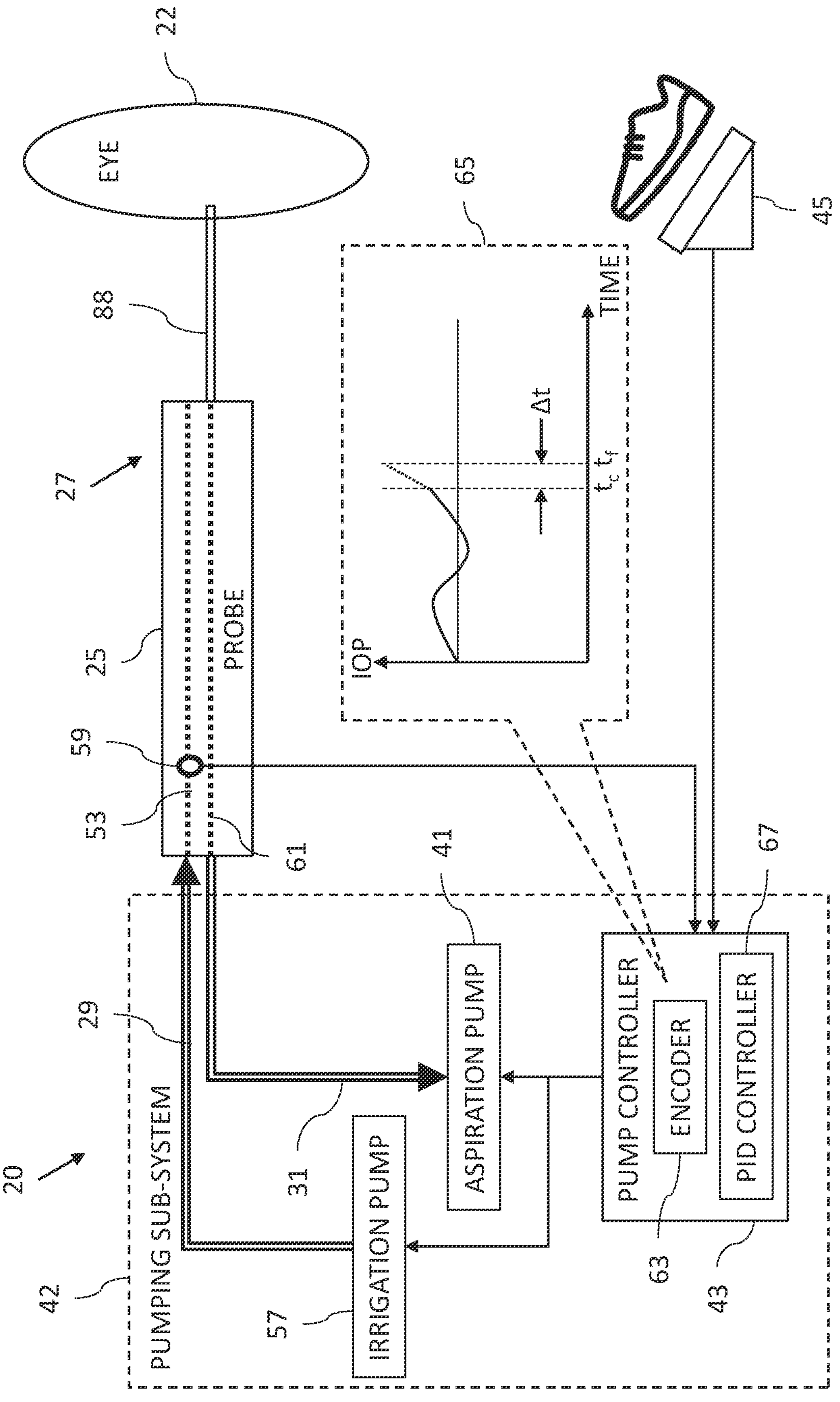
FIG. 2 is a block diagram view of part of the system of FIG. 1.

Reference is now made to FIG. 2, which is a block diagram view of part of the system 20 of FIG. 1. The tool 55 includes a phacoemulsification probe 25 having a distal end 27 comprising the needle 88, and configured to be inserted into the eye 22. The system 20 includes an irrigation tube 29 that extends into probe 25 to provide irrigation fluid into the eye 22. The phacoemulsification probe 25 also includes an irrigation channel 53 configured to be connected to the irrigation tube 29 and to carry irrigation fluid from the irrigation tube 29 to the distal end 27. The system 20 includes an irrigation pump 57 configured to be connected to the irrigation tube 29 and to pump irrigation fluid into the eye 22.

The system 20 also includes a sensor 59 (e.g., pressure sensor) configured to provide a signal indicative of current intraocular pressure in the eye 22. In some exemplary modes, the sensor 59 is disposed in the irrigation channel 53. In other exemplary modes the sensor 59 may be placed at the surgical site, for example on an additional probe that is concurrently positioned within eye 22.

The system 20 also includes an aspiration tube 31 configured to be connected to probe 25 and to convey aspiration fluid from the eye 22. The phacoemulsification probe 25 also includes an aspiration channel 61 to carry aspiration fluid from the eye 22 to the aspiration tube 31. The aspiration channel 61 extends from the distal end of the needle 88 to the proximal end of the phacoemulsification probe 25. The system 20 includes an aspiration pump 41 configured to be connected to the aspiration tube 31 and to pump the aspiration fluid from the eye 22.

The system 20 includes a pump controller 43 configured to control respective flow directions and flow rates of the aspiration pump 41 and the irrigation pump 57. In some exemplary modes, the pump controller 43 includes a proportional-integral-derivative (PID) controller 67, which is configured to control the irrigation pump 57 and the aspiration pump 41 responsively to control parameters.

The irrigation pump 57, aspiration pump 41, and pump controller 43 are comprised in the pumping sub-system 42. In some embodiments, the aspiration pump 41 and/or irrigation pump 57 may be a progressive cavity pump (PCP). For a PCP, the flow rate through the PCP is known based on the rotation of the rotor (e.g., revolutions per minute (RPM)).

In some exemplary modes, the pump controller 43 includes an encoder 63, which is configured to provide the flow rate (e.g., RPM) of the aspiration pump 41 and/or the irrigation pump 57 to the pump controller 43 intermittently and/or upon request.

FIG. 2 shows an inset 65 which shows an example graph of IOP against time. The graph shows the value of the IOP at the current time, $t_c$, based on the signal provided by the sensor 59. The inset 65 also shows the predicted (computed) IOP at a future time, $t_f$. The predicted IOP is described in more detail with reference to FIG. 3. The time difference, $\Delta t$, between $t_c$ and $t_f$ may be any suitable time depending on the reaction time of the irrigation pump 57 to adjust to a new flow rate and the compliance of the tubing of the irrigation tube 29, for example, to propagate the new flow rate to the phacoemulsification probe 25 and the eye 22. It is estimated that $\Delta t$ is about 100 milliseconds. In some cases, $\Delta t$ may be in the range of 50-200 milliseconds depending on the responsiveness of the irrigation pump 57 and the irrigation tube 29 and irrigation channel 53.

The pressure and/or flow rate provided by aspiration pump 41 may be selectively adjusted by a user with a user interface device 45, e.g., foot pedal. Pump controller 43 receives a command from user interface device 45 and controls the flow direction and flow rate of the aspiration pump 41 based on the command received. User input device 45 may include one or more of the following: a gyroscope, a variable resistor, and/or a strain gauge, by way of example for sensing input from the user. In some exemplary modes, when the user interface device is a foot pedal, the flow rate is adjusted based on the user pressing or releasing the foot pedal. Optionally, user interface device 45 is a virtual device on a display screen.

In practice, some or all of the functions of the pump controller 43 may be combined in a single physical component or, alternatively, implemented using multiple physical components. These physical components may comprise hard-wired or programmable devices, or a combination of the two. In some exemplary modes, at least some of the functions of the pump controller 43 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Figure 3:
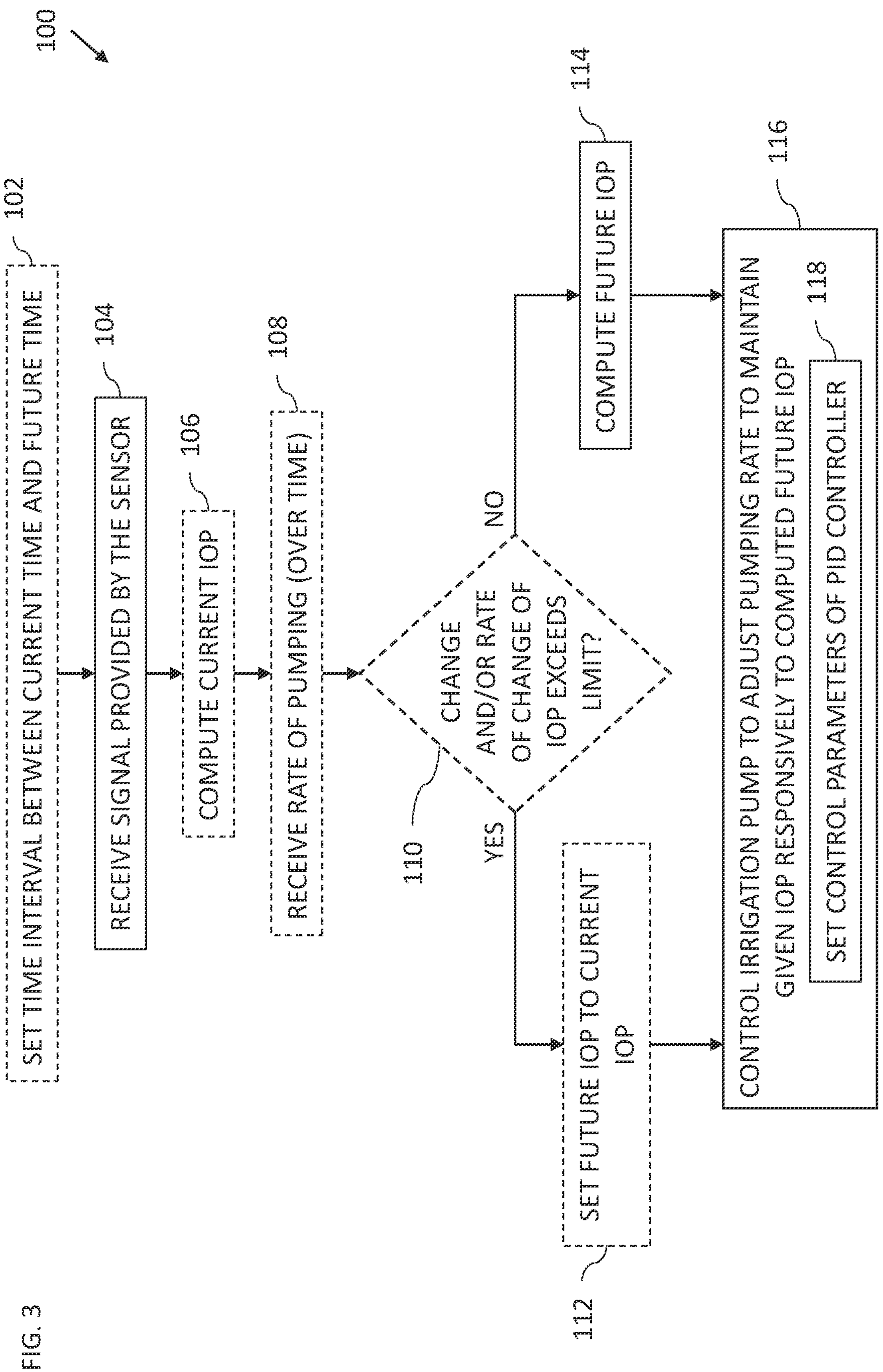
FIG. 3 is a flowchart including steps in a method of operation of the system of FIG. 1.

Reference is now made to FIG. 3, which is a flowchart 100 including steps in a method of operation of the system 20 of FIG. 1. In some exemplary modes, the pump controller 43 is configured to set the time interval between the current time and future time at which to compute the predicted value of the IOP (block 102). As previously mentioned, the time difference, Δt, between $t_c$ and $t_f$ may be any suitable time depending on the reaction time of the irrigation pump 57 to adjust to a new flow rate and the compliance of the tubing of the irrigation tube 29, for example, to propagate the new flow rate to the phacoemulsification probe 25 and the eye 22. It is estimated that Δt is about 100 milliseconds. In some cases, Δt may be in the range of 50-200 milliseconds.

The pump controller 43 is configured to receive the signal provided by the sensor 59 (block 104). In some exemplary modes, the pump controller 43 is configured to compute the current intraocular pressure responsively to the provided signal (block 106).

In some exemplary modes, when the aspiration pump is a PCP, the flow rate of the aspiration fluid is based on an RPM of PCP rotor. The encoder 63 is configured to provide the flow rate to the pump controller 43. Therefore, the pump controller 43 is configured to receive the flow rate from the encoder 63 over time (block 108). The flow rate of the aspiration fluid may be used in the computation of the IOP at the future time as described in more detail below. Additionally, or alternatively, the rate of change of the flow rate of the aspiration fluid may be used in the computation of the TOP at the future time as described in more detail below.

In some exemplary modes, if the TOP is changing too quickly, the predicted TOP may not be an accurate reflection of the actual future TOP and therefore, the predictive feature may be turned off. Therefore, optionally, at a decision block 110, the pump controller 43 determines if the change and/or rate of change of TOP and/or the aspiration flow rate exceeds a given limit (or limits). If the change and/or rate of change of TOP and/or aspiration flow rate exceeds the given limit(s) then the TOP at the future time computed from the change and/or rate of change of TOP and/or the aspiration flow rate may not provide useful results. Therefore, if the change and/or rate of change of TOP and/or the aspiration flow rate exceed the given limit(s) the pump controller 43 is configured to set the future TOP to be equal to the current computed TOP (block 112). If the change and/or rate of change of IOP and/or the aspiration flow rate does not exceed the given limit(s), the pump controller 43 is configured to compute the future TOP as described in more detail below (block 114). The given limits may be determined by observing over a period of time, the computed value of the TOP at the future time and the actual values of the TOP at the future time and the various factors contributing to the computed value of the TOP at the future time.

The pump controller 43 is configured to compute the value of intraocular pressure at the future time responsively to the provided signal and an indicator of change in the intraocular pressure over time. In some exemplary modes, the pump controller 43 is configured to compute the value of the intraocular pressure at the future time responsively to the computed current intraocular pressure and the indicator of change in the intraocular pressure over time.

In some exemplary modes, the pump controller 43 is configured to compute the value of the intraocular pressure at the future time responsively to the provided signal (or the computed current intraocular pressure) and at least one of the following: a flow rate of the aspiration fluid; a rate of change of the flow rate of the aspiration fluid; a change of the intraocular pressure over time; and a rate of change of the intraocular pressure over time.

For example, the TOP at the future time may be computed as a function of:

(i) Current TOP as computed from the signal of the sensor 59; plus (ii) A×the rate of change of IOP (given by previously computed IOPs); plus (iii) B×the aspiration fluid flow rate; plus (iv) C×the rate of change of the aspiration fluid flow rate.

A, B and C are parameters which may be set and adjusted based on comparing computed IOPs at future times and actual IOPs at the respective future times so as to minimize the difference over time between the computed future IOPs and the actual IOPs at the respective future times. In some exemplary modes, one or two of the parameters may set to zero.

The pump controller 43 is configured to control the irrigation pump 57 to adjust a flow rate of the irrigation fluid to maintain the intraocular pressure at a given intraocular pressure (e.g., a default IOP or an IOP set by the physician) responsively to the computed value of the intraocular pressure at the future time (block 116). In some exemplary modes, the pump controller 43 is configured to set control parameters of the proportional-integral-derivative (PID) controller 67 responsively to the given intraocular pressure and the computed value of the intraocular pressure at the future time (block 118).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 72% to 108%.

EXAMPLES

Example 1: A phacoemulsification system, comprising: a phacoemulsification probe having a distal end comprising a needle, and configured to be inserted into an eye; an irrigation tube configured to be connected to the probe and to provide irrigation fluid into the eye; an irrigation pump configured to be connected to the irrigation tube and to pump irrigation fluid into the eye; an aspiration tube configured to be connected to the probe and to convey aspiration fluid from the eye; an aspiration pump configured to be connected to the aspiration tube and to pump the aspiration fluid from the eye; a sensor configured to provide a signal indicative of current intraocular pressure in the eye; and a pump controller configured to: receive the signal provided by the sensor; compute a value of intraocular pressure at a future time responsively to the provided signal and an indicator of change in the intraocular pressure over time; and control the irrigation pump to adjust a flow rate of the irrigation fluid to maintain the intraocular pressure at a given intraocular pressure responsively to the computed value of the intraocular pressure at the future time.

Example 2: The system according to example 1, wherein the pump controller is configured to: compute the current intraocular pressure responsively to the provided signal; and compute the value of the intraocular pressure at the future time responsively to the computed current intraocular pressure and the indicator of change in the intraocular pressure over time.

Example 3: The system according to example 1, wherein the pump controller is configured to compute the value of the intraocular pressure at the future time responsively to the provided signal and at least one of: a flow rate of the aspiration fluid; a rate of change of the flow rate of the aspiration fluid; a change of the intraocular pressure over time; and a rate of change of the intraocular pressure over time.

Example 4: The system according to example 3, wherein the flow rate of the aspiration fluid is based on a flow rate of the aspiration fluid by the aspiration pump.

Example 5: The system according to example 4, wherein the pump controller includes an encoder, which is configured to provide the flow rate to the pump controller.

Example 6: The system according to example 1, wherein the future time is about 100 milliseconds from a current time.

Example 7: The system according to example 1, wherein the future time is between 50 and 200 milliseconds from a current time.

Example 8: The system according to example 1, wherein the phacoemulsification probe includes an irrigation channel configured to be connected to the irrigation tube, the sensor being disposed in the irrigation channel.

Example 9: The system according to example 1, wherein the pump controller includes a proportional integral derivative (PID) controller configured to control the irrigation pump responsively to control parameters, wherein the pump controller is configured to set the control parameters responsively to the given intraocular pressure and the computed value of the intraocular pressure at the future time.

Example 10: A phacoemulsification method, comprising: inserting a phacoemulsification probe having a distal end comprising a needle into an eye; pumping irrigation fluid into the eye via an irrigation tube connected to the probe; pumping aspiration fluid from the eye via an aspiration tube connected to the probe; receiving a signal indicative of current intraocular pressure in the eye; computing a value of intraocular pressure at a future time responsively to the signal and an indicator of change in the intraocular pressure over time; and adjusting a flow rate of the irrigation fluid to maintain the intraocular pressure at a given intraocular pressure responsively to the computed value of the intraocular pressure at the future time.

Example 11: The method according to example 10, further comprising computing the current intraocular pressure responsively to the signal, wherein computing the value includes computing the value of the intraocular pressure at the future time responsively to the computed current intraocular pressure and the indicator of change in the intraocular pressure over time.

Example 12: The method according to example 10, wherein the computing includes computing the value of the intraocular pressure at the future time responsively to the signal and at least one of: a flow rate of the aspiration fluid; a rate of change of the flow rate of the aspiration fluid; a change of the intraocular pressure over time; and a rate of change of the intraocular pressure over time.

Example 13: The method according to example 12, wherein the flow rate of the aspiration fluid is based on a flow rate of the aspiration fluid by an aspiration pump.

Example 14: The method according to example 13, further comprising an encoder provide the flow rate to the pump controller.

Example 15: The method according to example 10, wherein the future time is about 100 milliseconds from a current time.

Example 16: The method according to example 10, wherein the future time is between 50 and 200 milliseconds from a current time.

Example 17: The method according to example 10, wherein the sensor is disposed in an irrigation channel of phacoemulsification probe.

Example 18: The method according to example 10, further comprising setting control parameters of a proportional integral derivative (PID) controller responsively to the given intraocular pressure and the computed value of the intraocular pressure at the future time.

Various features of the disclosure which are, for clarity, described in the contexts of separate examples may also be provided in combination in a single example. Conversely, various features of the disclosure which are, for brevity, described in the context of a single example may also be provided separately or in any suitable sub-combination.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

What is claimed is:

1. A phacoemulsification system, comprising:

a phacoemulsification probe having a distal end comprising a needle, and configured to be inserted into an eye;

an irrigation tube configured to be connected to the phacoemulsification probe and to provide irrigation fluid into the eye;

an irrigation pump configured to be connected to the irrigation tube and to pump the irrigation fluid into the eye;

an aspiration tube configured to be connected to the phacoemulsification probe and to convey aspiration fluid from the eye;

an aspiration pump configured to be connected to the aspiration tube and to pump the aspiration fluid from the eye;

a sensor configured to provide a signal indicative of a current intraocular pressure in the eye; and a pump controller configured to:

receive the signal provided by the sensor;

compute a value of an intraocular pressure at a future time responsively to the signal and an indicator of change in the intraocular pressure over time; and control the irrigation pump to adjust a flow rate of the irrigation fluid to maintain the intraocular pressure at a given intraocular pressure responsively to the value of the intraocular pressure at the future time.

2. The system according to claim 1, wherein the pump controller is configured to:

compute the current intraocular pressure responsively to the signal; and compute the value of the intraocular pressure at the future time responsively to the current intraocular pressure and the indicator of change in the intraocular pressure over time.

3. The system according to claim 1, wherein the pump controller is configured to compute the value of the intraocular pressure at the future time responsively to the signal and at least one of: a flow rate of the aspiration fluid; a rate of change of the flow rate of the aspiration fluid; a change of the intraocular pressure over time; and a rate of change of the intraocular pressure over time.

4. The system according to claim 3, wherein the flow rate of the aspiration fluid is based on a flow rate of the aspiration fluid by the aspiration pump.

5. The system according to claim 4, wherein the pump controller includes an encoder, which is configured to provide the flow rate of the aspiration fluid to the pump controller.

6. The system according to claim 1, wherein the future time is about 100 milliseconds from a current time.

7. The system according to claim 1, wherein the future time is between 50 and 200 milliseconds from a current time.

8. The system according to claim 1, wherein the phacoemulsification probe includes an irrigation channel configured to be connected to the irrigation tube, the sensor being disposed in the irrigation channel.

9. The system according to claim 1, wherein the pump controller includes a proportional integral derivative (PID) controller configured to control the irrigation pump responsively to control parameters, wherein the pump controller is configured to set the control parameters responsively to the given intraocular pressure and the value of the intraocular pressure at the future time.

10. A phacoemulsification method, comprising:

inserting a phacoemulsification probe having a distal end comprising a needle into an eye;

pumping irrigation fluid into the eye via an irrigation tube connected to the phacoemulsification probe;

pumping aspiration fluid from the eye via an aspiration tube connected to the phacoemulsification probe;

receiving, from a sensor, a signal indicative of a current intraocular pressure in the eye;

computing, by a pump controller, a value of an intraocular pressure at a future time responsively to the signal and an indicator of change in the intraocular pressure over time; and adjusting a flow rate of the irrigation fluid to maintain the intraocular pressure at a given intraocular pressure responsively to the value of the intraocular pressure at the future time.

11. The method according to claim 10, further comprising computing the current intraocular pressure responsively to the signal, wherein the computing the value includes computing the value of the intraocular pressure at the future time responsively to the current intraocular pressure and the indicator of change in the intraocular pressure over time.

12. The method according to claim 10, wherein the computing includes computing the value of the intraocular pressure at the future time responsively to the signal and at least one of: a flow rate of the aspiration fluid; a rate of change of the flow rate of the aspiration fluid; a change of the intraocular pressure over time; and a rate of change of the intraocular pressure over time.

13. The method according to claim 12, wherein the flow rate of the aspiration fluid is based on a flow rate of the aspiration fluid by an aspiration pump.

14. The method according to claim 13, further comprising an encoder to provide the flow rate of the aspiration fluid to the pump controller.

15. The method according to claim 10, wherein the future time is about 100 milliseconds from a current time.

16. The method according to claim 10, wherein the future time is between 50 and 200 milliseconds from a current time.

17. The method according to claim 10, wherein the sensor is disposed in an irrigation channel of the phacoemulsification probe.

18. The method according to claim 10, further comprising setting control parameters of a proportional integral derivative (PID) controller of the pump controller responsively to the given intraocular pressure and the computed value of the intraocular pressure at the future time.

* * * * *